(12) United States Patent
Holcombe

(10) Patent No.: US 9,029,098 B1
(45) Date of Patent: May 12, 2015

(54) DATE-RAPE DRUG DETECTOR

(71) Applicant: Kathy Barbosa Holcombe, Carrollton, TX (US)

(72) Inventor: Kathy Barbosa Holcombe, Carrollton, TX (US)

( * ) Notice: Subject to any disclaimer, the term of this patent is extended or adjusted under 35 U.S.C. 154(b) by 0 days.

(21) Appl. No.: 14/156,249

(22) Filed: Jan. 15, 2014

Related U.S. Application Data

(60) Provisional application No. 61/753,541, filed on Jan. 17, 2013.

(51) Int. Cl.
*C12Q 1/26* (2006.01)
*C12M 1/40* (2006.01)
*G01N 21/77* (2006.01)

(52) U.S. Cl.
CPC .......... *C12Q 1/26* (2013.01); *G01N 2021/7759* (2013.01)

(58) Field of Classification Search
IPC ............................. C12Q 1/26; G01N 2021/7759
See application file for complete search history.

(56) References Cited

U.S. PATENT DOCUMENTS

| | | | |
|---|---|---|---|
| 5,071,623 A * | 12/1991 | Akutsu | 422/420 |
| 8,563,317 B2 | 10/2013 | Grossman et al. | |
| 2001/0046710 A1 | 11/2001 | Cutler | |
| 2003/0044989 A1 | 3/2003 | Guerra et al. | |
| 2003/0224474 A1 * | 12/2003 | Litman | 435/28 |
| 2008/0102482 A1 | 5/2008 | Grossman et al. | |
| 2010/0035332 A1 * | 2/2010 | Thomas | 435/287.1 |
| 2010/0081188 A1 | 4/2010 | Campbell et al. | |
| 2011/0039346 A1 | 2/2011 | Bradley et al. | |
| 2011/0195507 A1 | 8/2011 | Dancer | |
| 2012/0070901 A1 | 3/2012 | Bradley et al. | |
| 2013/0329216 A1 | 12/2013 | Patolsky et al. | |

FOREIGN PATENT DOCUMENTS

| GB | 2447899 A | * 10/2008 |
|---|---|---|
| GB | 2486472 A | * 12/2010 |

* cited by examiner

*Primary Examiner* — Sharmila G. Landau
*Assistant Examiner* — Paul Martin
(74) *Attorney, Agent, or Firm* — Kenneth L Tolar

(57) ABSTRACT

A date-rape drug detector includes an elongated shaft having an upper end and a lower end. The upper end of the shaft is bendable and includes a plurality of notches that grip the upper rim of a beverage container. Proximal the lower end is a chamber having a testing strip therein that is deployable to a perpendicular position relative to the shaft. Along the length of the strip are a plurality of reactive spots that change color in the presence of a date-rape drug. Each successive spot is covered with a progressively thicker layer of water-soluble material than a preceding spot so that each spot requires a different submersion time in order to be exposed. Therefore, a user can test a beverage for the presence of a date-rape drug at progressive intervals.

4 Claims, 2 Drawing Sheets

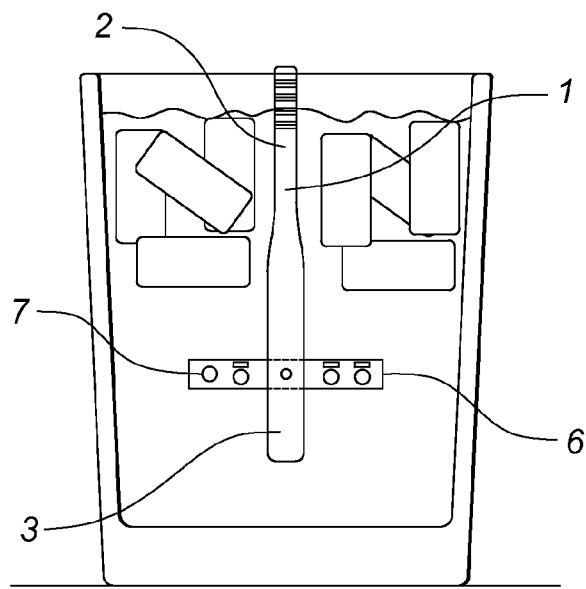
Fig. 1
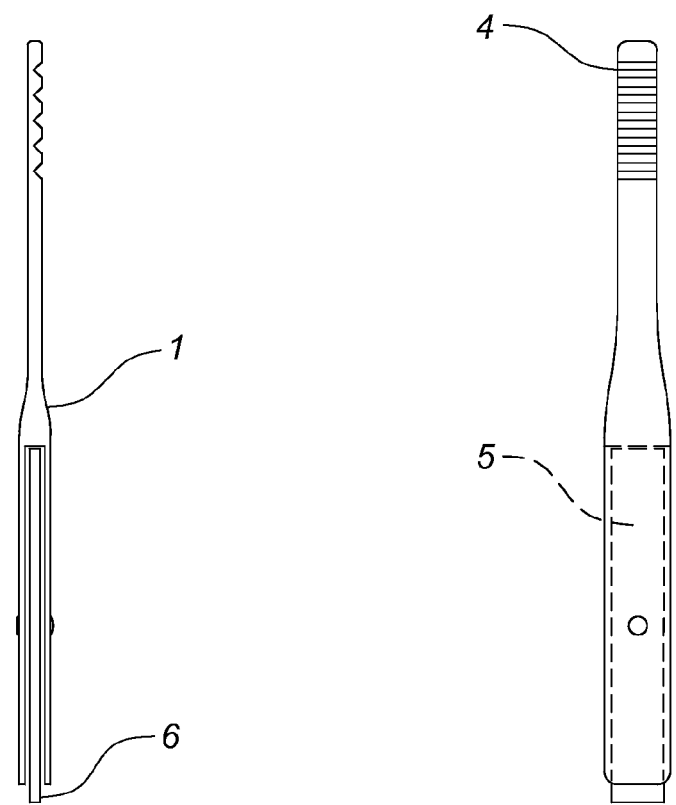
Fig. 2
Fig. 3

DATE-RAPE DRUG DETECTOR

CROSS REFERENCE TO RELATED APPLICATIONS

This application is entitled to the benefit of provisional patent application No. 61/753,541 filed on Jan. 17, 2013, the specification of which is incorporated herein by reference.

BACKGROUND OF THE INVENTION

The present invention relates to a detector for quickly determining whether a beverage has been spiked with a date-rape drug.

DESCRIPTION OF THE PRIOR ART

Date-rape drugs, such as GHB, Rhohypnol and Ketamine, can be easily and unknowingly slipped into an inattentive victim's drink. Because these drugs are tasteless, odorless and colorless, they are undetectable until the victim consumes the drugs and suffers their adverse effects. Once ingested, the drugs can cause severe drowsiness, dizziness, unconsciousness, hallucinations and sometimes comas or death. When under the influence of such drugs, the victim is defenseless to a sexual assault, a robbery or another crime. Accordingly, there is currently a need for a device that easily detects the presence of common date-rape drugs in a beverage.

A review of the prior art reveals a myriad of date-rape drug detectors. For example, U.S. Pat. No. 8,563,317 issued to Grossman et al. discloses a GHB detector for beverages comprising a substrate impregnated with various reagents.

U.S. published patent application no. 2001/0046710 to Cutler discloses a drug-detection device including a toothpick, a cotton swab or test strip having a reagent thereon that changes color in the presence of an illicit drug.

U.S. published patent application no. 2003/0044989 to Guerra et al. discloses a beverage-testing device including a porous substrate, such as a napkin, coaster or a business card, having colorimetric substances thereon.

U.S. published patent application no. 2008/0102482 to Grossman et al. discloses a beverage tester including a support having a plurality of strips extending therefrom. Each of the strips is configured to detect a specific type of drug.

U.S. published patent application no. 2011/0039346 to Bradley et al. discloses a straw coated with a color-changing reagent to detect certain date-rape drugs.

As indicated above, several detectors exist that change colors when exposed to certain drugs. However, the prior-art detectors can only test a beverage once, unless a new test strip is later used. Therefore, with the prior-art devices, a beverage is vulnerable to contamination from the time an initial test is performed until the beverage is completely consumed. Accordingly, there is currently a need for a device that allows a user to progressively test a beverage for contamination over a predetermined duration to prevent post-testing contamination.

The present invention addresses this need by providing a test strip having a plurality of reactive spots that each change color in the presence of a date-rape drug. Each successive spot is covered with a progressively-thicker layer of water-soluble material than a preceding spot so that each spot requires a different submersion time in order to be exposed. Therefore, a user can test a beverage for the presence of a date-rape drug at progressive intervals to verify that the beverage is safe until it is completely consumed.

SUMMARY OF THE INVENTION

The present invention relates to a date-rape drug detector comprising an elongated shaft having an upper end and a lower end. The upper end of the shaft is bendable and includes a plurality of notches that grip the rim of a beverage container. Proximal the lower end is a chamber having a testing strip therein that is deployable to a perpendicular position relative to the shaft. Along the length of the strip are a plurality of reactive spots that change color in the presence of a date-rape drug. Each successive spot is covered with a progressively thicker layer of water-soluble material than a preceding spot so that each spot requires a different submersion time in order to be exposed. Therefore, a user can test a beverage for the presence of a date-rape drug at progressive intervals.

It is therefore an object of the present invention to provide a device for quickly and easily detecting the presence of a date-rape drug in a beverage.

It is another object of the present invention to provide a detector that allows a user to repeatedly test a beverage for the presence of a date-rape drug at progressive intervals.

Other objects, features, and advantages of the present invention will become readily apparent from the following detailed description of the preferred embodiment when considered with the attached drawings and the appended claims.

BRIEF DESCRIPTION OF THE DRAWINGS

FIG. 1 is a front, sectional view of a beverage container with the detector immersed therein.

FIG. 2 is an isolated, side view of the detector with the testing strip in a collapsed position.

FIG. 3 is an isolated, front view of the detector with the testing strip in a collapsed position.

DESCRIPTION OF THE PREFERRED EMBODIMENT

Figure 4:
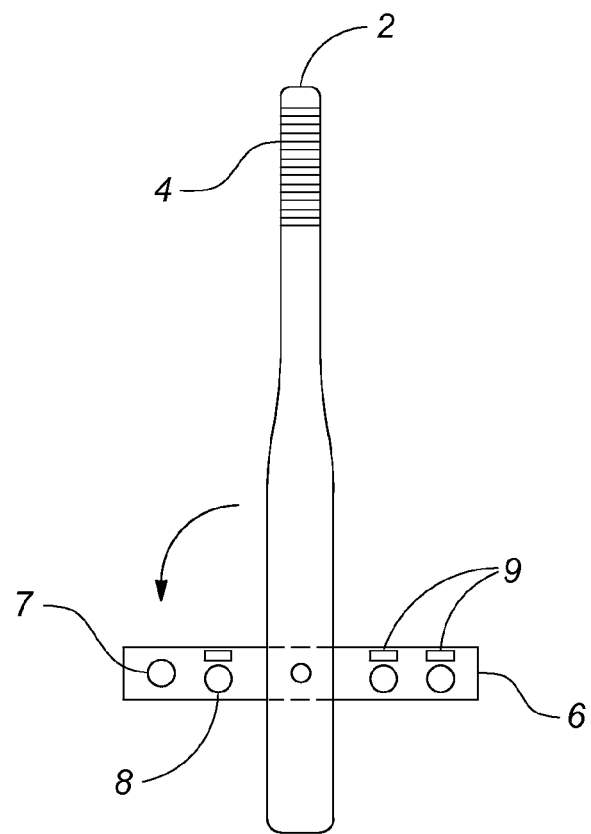
FIG. 4 is an isolated view of the detector with the testing strip in a deployed position.
Figure 5:
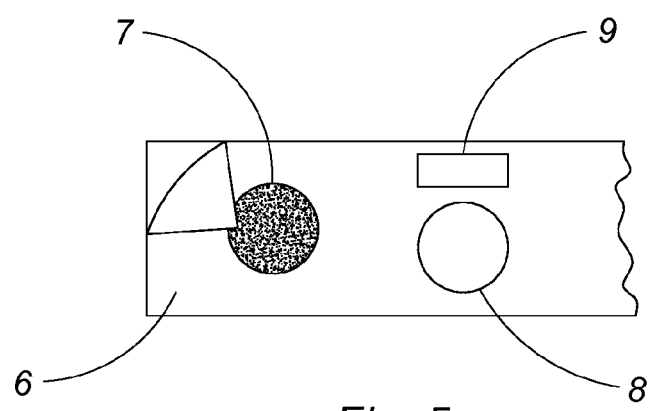
FIG. 5 is an isolated view of exemplary reactive spots.

The present invention relates to a date-rape drug detector comprising an elongated shaft 1 having an upper end 2 and a lower end 3. The upper end of the shaft is bendable to an angle of ninety degrees or more and includes a plurality of notches 4 that grip the rim of a beverage container. Proximal the lower end is a chamber 5 having a testing strip 6 therein that is deployable to a perpendicular position relative to the shaft. Along the length of the strip are a plurality of reactive spots that change color in the presence of a date-rape drug. A first spot 7 is exposed while the remaining, succeeding spots 8 are covered with a progressively thicker layer of water-soluble acetate.

Adjacent to each of the covered spots 8 is a rectangle 9 that changes color in the presence of liquid. Each of the rectangles is likewise covered with a progressively thicker layer of water-soluble material relative to a preceding rectangle, and which is equal to the thickness of the layer on the adjacent spot. Therefore, each spot and associated rectangle requires a different submersion time than the others in order to be exposed. Once a rectangle changes color (preferably to red), the user is readily alerted that the layer on the adjacent, corresponding spot has dissolved. The user then removes the strip to allow the spot to air dry in order to complete the reaction.

Accordingly, in order to detect the presence of a date-rape drug, a user deploys the testing strip and immerses the shaft into a beverage. The uncovered spot allows a user to immediately determine if the beverage contains a date-rape drug. The remaining spots allow a user to subsequently test the beverage at different times thereafter. For example, a second spot and associated rectangle may be exposed 5 minutes after immersion, a third spot and associated rectangle may be exposed 10 minutes after immersion, etc. If any of the exposed spots change to a predetermined color, then a date-rape drug is present and the drink is discarded. If an exposed spot's color remains unchanged, the drink is safe to consume.

The date-rape drug detection reagent preferably uses an enzymatic oxidation of GHB by NAD+ (Nicotinamide adenine dinucleotide) coupled with diaphorase-mediated reduction of pro-dye to yield a colored byproduct. The conventional laboratory process could be enhanced with a some experimentation in conjunction with a chemical supplier to provide solutions that are applied to the testing strip, dried, and then coated with the water-soluble acetate as described above. Products such as those currently marketed and sold by 2 Drink Safe Tech in the USA and Drink Spike Detector in Australia could be used. The water-detection reagent is a commercially-available product currently produced and sold by Novavision. However, any suitable reagent that changes color or appearance in the presence of illicit drugs could also be used.

Preferably, the spots, rectangles and water-soluble layers are applied to a sheet or substrate, which is adhesively bonded to the testing strip. The shaft is preferably constructed with a transparent material so that the detector is relatively indiscernible when submerged within a beverage. However, the above-described device is not limited to the exact details of construction and enumeration of parts provided herein. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A date-rape drug detector comprising:
   an elongated shaft having an upper end and a lower end;
   a plurality of spots at the lower end, each of said spots having a reagent thereon that changes color in the presence of a date-rape drug, one of said spots being exposed so that the reagent immediately contacts a beverage when submerged therein, the others of said plurality of spots being covered with progressively thicker water-soluble layers that dissolve after being submerged in the beverage for a predetermined time period to allow a user to test the beverage at progressive time intervals.

2. The date-rape drug detector according to claim 1 wherein the upper end of the shaft is bendable and includes a plurality of notches that grip an upper rim of a beverage container.

3. The date-rape drug detector according to claim 1 wherein said spots are positioned on a testing strip that is collapsible into a chamber at the lower end of said shaft, and deployable to a perpendicular position relative to said shaft.

4. The date-rape drug detector according to claim 1 where the other of said spots has a rectangle adjacent thereto, said rectangle having a reagent thereon that changes color in the presence of liquid, said rectangle covered with a layer of water-soluble material that is equal to the thickness of the water-soluble layers covering the others of said spots.

* * * * *